United States Patent [19]
De Valois et al.
[11] Patent Number: 4,749,682
[45] Date of Patent: Jun. 7, 1988

[54] PERFUME COMPOSITIONS AND PERFUMED PRODUCTS WHICH CONTAIN AN ALKYL 2-MERCAPTOBENZOATE AS FRAGRANCE MATERIAL

[75] Inventors: Pieter J. De Valois, Naarden; Theo Heideman, Huizen; Hans J. Wille, Bussum; Henry L. A. Van Den Heuvel, Hilversum, all of Netherlands

[73] Assignee: Naarden International N.V., Netherlands

[21] Appl. No.: 912,768

[22] Filed: Sep. 26, 1986

[30] Foreign Application Priority Data

Oct. 22, 1985 [NL] Netherlands ........................ 8502884

[51] Int. Cl.[4] ........................ A61K 7/46
[52] U.S. Cl. ........................ 512/20; 252/174.11; 424/65; 424/76.4
[58] Field of Search ......... 560/18; 252/522 R, 174.11; 512/20; 424/65, 76

[56] References Cited

U.S. PATENT DOCUMENTS 3,729,508 4/1973 Ziegler et al. ........................ 560/18
3,984,573 1/1976 Naipower et al. ........................ 426/3
4,469,874 9/1984 Maender ........................ 560/18

OTHER PUBLICATIONS

Margalith, "Flavor Microbiology", p. 19 (1981).

*Primary Examiner*—James H. Reamer
*Attorney, Agent, or Firm*—Brumbaugh, Graves, Donohue & Raymond

[57] ABSTRACT

Perfume compositions and perfumed products characterized by a content of one or more fragrances having a long-lasting flowery and somewhat spicy odor with a not very pronounced sulphurous note and corresponding to the formula

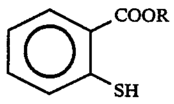

(1)

wherein R represents a methyl or ethyl group.

6 Claims, No Drawings

PERFUME COMPOSITIONS AND PERFUMED PRODUCTS WHICH CONTAIN AN ALKYL 2-MERCAPTOBENZOATE AS FRAGRANCE MATERIAL

The invention relates to perfume compositions which contain an alkyl 2-mercaptobenzoate and to products perfumed with these compounds or with said compositions.

There is a continuing interest in the preparation and use of synthetic fragrance materials and the use thereof in products to be perfumed. Said interest is stimulated by the inadequate quantity and often changing quality of natural fragrance materials.

Although sulphur compounds usually do not have a pleasant odor it has nevertheless emerged that they play an essential role in many natural odor complexes. Therefore there is a need for compounds with a "sulphurous" odor note which is clearly present but is not too prominent, preferably combined with other, pleasant odor notes so that the compounds can readily be combined with known fragrance materials.

Surprisingly, it has now been found that alkyl 2-mercaptobenzoates having the following general formula:

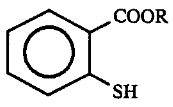

wherein R represents a methyl or ethyl group, are valuable and powerful fragrances. The compounds have a very long-lasting flowery and, to some extent, spicy odor with a not very pronounced sulphurous note.

In relation to the compounds according to the invention, U.S. Pat. No. 3,984,573 states that they are suitable for improving concord grape aroma by intensifying the meaty and breadlike character therein. It was not possible, however, to conclude from this that the compounds would be suitable as fragrance materials or that they would have a flowery-spicey odor character.

The compounds according to the invention can be prepared by methods known in the literature, for example, as described in the above-mentioned U.S. Patent, in particular in Examples I and II.

The compounds can be used as such as fragrances, or they can first be mixed with suitable carriers or diluants. However, they will preferably be combined with other individual compounds or with mixtures such as essential oils to form perfume compositions in the manner usual for the preparation of such compositions.

In this connection the term "perfume composition" is understood to mean a mixture of fragrance materials and optionally auxiliary substances, that may be dissolved in a suitable solvent or mixed with a powdery substrate and used to impart a desired odor to the skin and/or to various products. Examples of such products are: soaps, detergents, air fresheners, room sprays, pomanders, candles, cosmetics such as creams, ointments, toilet waters, pre- and aftershave lotions, talcum powders, hair-care products, body deodorants and anti-perspirants.

Fragrance materials and mixtures thereof which can be used in combination with the compounds according to the invention for the preparation of perfume compositions are e.g. natural products such as essential oils, absolutes, resinoids, resins, concretes etc., but also synthetic fragrance materials such as hydrocarbons, alcohols, aldehydes, ketones, ethers, acids, esters, acetyls, ketyls, nitriles etc., including saturated and unsaturated compounds, aliphatic, carbocyclic and heterocyclic compounds. Examples of fragrance materials which can be used in combination with the compounds according to the invention are: geraniol, geranyl acetate, linalool, linalyl acetate, tetrahydrolinalool, citronellol, citronellyl acetate, dihydro myrcenol, dihydro myrcenyl acetate, tetrahydro myrcenol, terpineol, terpinyl acetate, nopol, nopyl acetate, 2-phenylethanol, 2-phenylethyl acetate, benzyl alcohol, benzyl acetate, benzyl salicylate, styrallyl acetate, benzyl benzoate, amyl salicylate, dimethylbenzylcarbinol, trichloromethyl-phenyl-carbinyl acetate, p-tert-butylcyclohexyl acetate, isononyl acetate, vetiveryl acetate, vetiverol, α-hexylcinnamaldehyde, 2-methyl-3-(p-tert-butylphenyl)propanal, 2-methyl-3-(p-isopropylphenyl)-propanal, 3-(p-tert-butylphenyl)propanal, tricyclodecenyl acetate, tricyclodecenyl propionate, 4-(4-hydroxy-4-methylpentyl)-3-cyclohexene carbaldehyde, 4-(4-methyl-3-pentenyl)-3-cyclohexene carbaldehyde, 4-acetoxy-3-pentyl-tetrahydropyran, 3-carboxymethyl-2-pentylcyclopentane, 2-n-heptylcyclopentanone, 3-methyl-2-pentyl-2-cyclopentanone, n-decanal, n-dodecanal, 9-decenol-1, phenoxyethyl isobutyrate, phenylacetaldehyde dimethylacetyl, phenylacetaldehyde diethylacetyl, geranyl nitrile, citronellyl nitrile, cedryl acetate, 3-isocamfylcyclohexanol, cedryl methyl ether, isolongifolanone, aubepine nitrile, aubepine, heliotropine, coumarin, eugenol, vanillin, diphenyl oxide, hydroxycitronellal, iones, methylionones, isomethylionones irones, cis-3-hexenol and esters thereof, indan-musks, tetralin-musks, isochroman-musks, macrocyclic ketones, macrolactone musks, ethylene brassylate, aromatic nitromusks.

Auxiliary substances and solvents which can be used in perfume compositions which contain compounds according to the invention are e.g.: ethanol, isopropanol, diethylene glycol monoethyl ether, diethyl phthalate, etc.

The quantities in which the compounds according to the invention can be used in perfume compositions or products to be perfumed may vary within wide limits and depend, inter alia, on the nature of the product in which the fragrance is used, on the nature and the quantity of the other compounds in the perfume composition and on the intended odor effect. For this reason it is only possible to give rough limits, but this provides sufficient information for those skilled in the art to be able to use the compounds according to the invention independently. In most cases a quantity of only 0.01% by weight in a perfume composition will already be sufficient to obtain a clearly perceptible odor effect. On the other hand, in order to achieve special odor effects, it is possible to use quantities of 10% by weight or even more in a composition. In products perfumed by means of perfume compositions said concentrations are proportionately lower, depending on the quantity of composition used in the product.

The following examples serve solely to illustrate the preparation and use of the compounds according to the invention. The invention is not, however, limited thereto.

EXAMPLE I

A perfume composition of the floral type was prepared according to the recipe below:

| | |
|---|---|
| Hydroxycitronellal | 100 parts by weight |
| Methyl dihydrojasmonate | 100 parts by weight |
| α-pentylcinnamaldehyde | 100 parts by weight |
| Citronellol | 100 parts by weight |
| Benzyl acetate | 50 parts by weight |
| Acetyl-cedrene | 50 parts by weight |
| Lemon oil | 50 parts by weight |
| 11-oxahexadecanolide | 30 parts by weight |
| Citronellyl acetate | 30 parts by weight |
| Bergamot oil | 30 parts by weight |
| Cinnamyl alcohol | 25 parts by weight |
| Benzylisoeugenol | 25 parts by weight |
| Jasmin absolute, Italian* | 20 parts by weight |
| γ-methylionone | 20 parts by weight |
| 3-phenylpropan-1-ol | 10 parts by weight |
| Heliotropine | 10 parts by weight |
| Rose oil, Moroccan* | 10 parts by weight |
| Methyl 2,4-dihydroxy-3,6-dimethyl-benzoate | 5 parts by weight |
| 4-(tricyclo[5.2.1.$0^{2,6}$]dec-8-ylidene)-butanal | 5 parts by weight |
| Prenyl acetate | 5 parts by weight |
| Allyl 3-methylbutoxy-acetate* | 5 parts by weight |
| Methyl 2-mercaptobenzoate* | 20 parts by weight |
| TOTAL | 800 parts by weight |

*10% solution in dipropylene glycol

What is claimed is:

1. Perfume compositions having a floral note consisting essentially of fragrance materials, including, an effective odorant amount of one or both compounds having the formula

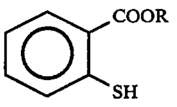

(1)

wherein R represents a methyl or ethyl group, and at least one customary auxiliary substance.

2. A perfume composition according to claim 1, wherein one or both compounds having formula (1) are present at a level of at least 0.01% by weight.

3. A perfumed product selected from the group consisting of soaps, detergents, air fresheners, room sprays, pomanders, candles, cosmetics, ointments, toilet waters, pre- and aftershave lotions, talcum powders, hair care products, body deodorants and antiperspirants comprising an effective odorant amount of one or both compounds having the formula

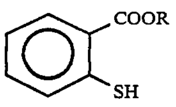

(1)

wherein R represents a methyl or ethyl group.

4. A method of imparting a floral note to a perfumed product comprising adding to the product an effective odorant amount of one or both compounds of the formula

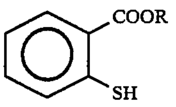

(1)

wherein R represents a methyl or ethyl group.

5. A method of imparting a floral note to a perfume composition comprising adding to the perfume composition an effective odorant amount of one or both compounds of the formula

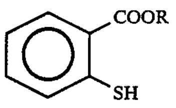

(1)

wherein R represents a methyl or ethyl group.

6. A method according to claim 5, wherein the compounds of formula (1) are added at a level of at least 0.01% by weight to the perfume composition.

* * * * *